United States Patent [19]

Lee et al.

[11] Patent Number: 5,407,579
[45] Date of Patent: Apr. 18, 1995

[54] HEMOGLOBIN PURIFICATION

[75] Inventors: Chau-Jen Lee; Pei Kan, both of Hsinchu, Taiwan, Prov. of China

[73] Assignee: National Science Council, Taipei, Taiwan, Prov. of China

[21] Appl. No.: 86,712

[22] Filed: Jul. 2, 1993

[51] Int. Cl.$^6$ .................... B01D 11/00; B01D 61/00; B01D 21/26; A61K 35/14
[52] U.S. Cl. ................... 210/634; 210/639; 210/645; 210/782; 210/789; 436/177; 436/178; 530/385; 530/412; 530/422; 530/427
[58] Field of Search ............... 210/634, 635, 639, 644, 210/645, 782, 789, 723, 724, 729; 436/177, 178; 530/385, 421, 422, 427, 412, 417; 536/25.41

[56] References Cited

U.S. PATENT DOCUMENTS

| | | | |
|---|---|---|---|
| 3,897,414 | 7/1975 | Albertsson | 536/25.41 |
| 4,401,652 | 8/1983 | Simmonds et al. | 530/385 |
| 4,645,829 | 2/1987 | Ho | 530/412 |
| 5,078,886 | 1/1992 | Hsu | 210/634 |
| 5,114,589 | 5/1992 | Shibusawa et al. | 210/634 |
| 5,264,555 | 11/1993 | Shorr et al. | 530/385 |

OTHER PUBLICATIONS

S. M. Christensen et al., Journal of Biochemical and Biophysical Methods, 17 (1988) 143–154.
T. I. Pristoupil et al., International Journal of Artificial Organs, vol. 13, No. 8 (1990) 383–387.
L. C. Cheung et al., Analytical Biochemistry, 137, 481–484 (1984).
J. R. DeLoach et al., Analytical Biochemistry, 137, 191–198 (1986).
P. Albertsson, Biochimica Et Biophysica Acta, vol. 27 (1958) 378–395.
H. Hustedt et al., Biotechnology and Bioengineering, vol. XX (1978) 1989–2005.
S. F. Rabiner et al., J. Exp. Med., 126, 1127–1142 (1967).
F. DeVenuto et al., J. Lab. Clin. Med., 89, 509–516 (1977).
T. Brittain, Journal of Chemical Education, vol. 59, No. 3 (1982) 253–255.

*Primary Examiner*—Sun Uk Kim
*Attorney, Agent, or Firm*—W. Wayne Liauh

[57] ABSTRACT

Disclosed is an improved method for hemoglobin purification utilizing a novel two-step dual-aqueous-phase extraction technique to separate hemoglobin from red cell membrane stroma and other protein contaminants. In the first step, a first dual-aqueous-phase liquid system is prepared which comprises an upper aqueous phase containing polyethylene glycol in water and a lower aqueous phase containing a phosphate buffer at a pH of about 10. In the second step, a second dual-aqueous-phase liquid system is prepared which comprises an upper aqueous phase, which contains the polyethylene glycol phase containing the hemoglobin extracted in the first step, and a lower aqueous phase containing a new phosphate buffer at a pH of less than 7.5. After the second extraction step, purified hemoglobin solution can then be obtained by removing the phosphate salt and the minute amounts of polyethylene glycol contained in the lower phase.

8 Claims, 9 Drawing Sheets

Hemolysate →
Carbonic Anhydrase →

1   2   3   4

1 2 3

1 2 3 4 5 6 7 8

HEMOGLOBIN PURIFICATION

FIELD OF THE INVENTION

This invention relates to a method of hemoglobin purification. More particularly, the present invention relates to a novel method for removing stromal particles and phospholipids from human outdated blood and animal bloods to obtain purified hemoglobin, which can be used in substitute blood applications.

BACKGROUND OF THE INVENTION

Blood substitute has recently received a great deal of attention due to its potential application to solving the blood shortage problems as well as providing an expeditious means allowing blood transfusion during wars or other emergency situations. Blood substitute can also find applications in many other situations, such as in preventing the spreading of diseases such as AIDS, hepatitis B, etc.; in the treatment of certain blood diseases; for organ preservation prior to organ transplants: in animal blood transfusion; as well as in perfusion for artificial organs.

In order to serve the above indicated functions, a blood substitute must provide the essential capacity to carry and release oxygen in an animal body. Current research attention in the development of suitable blood substitute has been focusing on utilizing hemoglobin as the base material, by reprocessing the same using polymerization or encapsulation technique so that it can be used. There have also been research efforts in developing plasma substitutes prepared from artificially synthesized oxygen-carrying material. However, at the present time, the artificially prepared oxygen-carrying material has not been able to provide the same level of functionality as the naturally occurring hemoglobin, and thus is unable to satisfy the physiological oxygen transport requirement in animal bodies.

Hemoglobin existing in outdated human or animal bloods has been under continuous evaluation for its potential application as a blood substitute. Separation and purification of hemoglobin from mammalian bloods and reprocessing them into oxygen carrying red blood cells provide an immense potential in supplying large quantities of blood substitute. Regardless of its source, the hemoglobin must go through a series of separation steps to remove protein contaminants and stroma (containing phospholipids), which, among other things, can stimulate human body and cause undesirable side effects, and thus increase the purity of hemoglobin.

A number of methods for hemoglobin purification have been available in the course of the development of blood substitute. In the early stages, high-speed centrifugation and ultrafiltration were the most widely used techniques. These methods, however, can only provide a very crude separation; many contaminants still exist in the hemoglobin solution after the purification treatment.

In 1967, Rabiner developed a method for hemoglobin purification, Rabiner, S. F., et al.: *Evaluation of a stroma-Free hemoglobin solution for use as a plasma expander, J. Exp. Med.* 126, 1127–1142 (1967). First, red blood cells were separated from outdated human whole blood by centrifugation and then washed with saline. Distilled water or organic solvents with low osmotic pressure were then added thereto to hemolyze the red blood cells. Hemoglobin would be released as a result of hemolysis of the red blood cells. Then the solution was subject to a high-speed centrifugation at 35,000 g to precipitate and remove cell membrane stroma. Finally the solution was filtered through 0.1 µm filter membrane to obtain purified hemoglobin. The Rabiner method is only capable of removing stromal particles that are relatively large; it, however, does not remove other proteins in the red blood cell and smaller cell membrane particles.

Drabkin and DeVenuto respectively developed crystallization methods for hemoglobin purification, both of which involved the first step of separating plasma and washing blood cells see, DeVenuto, F., et al.: *Characteristics of stroma-free hemoglobin prepared by crystallization, J. Lab. Clin. Med.* 89: 509–16 (1977). Then the red blood cells were hemolyzed to release hemoglobin. A relatively low-speed centrifugation, at 4,000 g, was applied to the hemolysate to remove relatively larger stromal particulate matter. Then a high concentration phosphate buffer was added to the solution to salt out hemoglobin, which is then subject to a crystal growth to obtain high purity hemoglobin. Because the crystal growth is a very time-consuming process, mass production utilizing this technique is difficult, and it is not practical to use this process to obtain large amount of high purity hemoglobin.

Cheung in 1983 utilized the principle of chromatography to develop a technique for hemoglobin purification using DEAE cellulose. In an article entitled "The Preparation of Stroma-Free Hemoglobin by Selective DEAE-Cellulose Absorption," Analytical Biochemistry 137, 481–484 (1984), by Cheung et al., it is disclosed that DEAE-Cellulose was used to absorb negatively charged proteins. By controlling the solution pH at a basic value (pH 7.5), proteins with an isoelectric point (pI) of far less than 7.5 can be selectively absorbed on the cellulose. On comparison, hemoglobin, which has a pI of about 7 and is only slightly negatively charged, will not be absorbed by the cellulose. Therefore, after mixing and absorption reach equilibrium and a series of filtration steps to remove the stroma-containing cellulose, purified hemoglobin can be obtained. However, because cellulose resins are relatively expensive, this process is not economical in practical applications, unless the cellulose resins can be reused.

In an article entitled "A Continuous-Flow High-Yield Process for Preparation of Lipid-Free Hemoglobin," Analytical Biochemistry 137, 191–198 (1986), DeLoach proposed a technique which combined dialysis and ultrafiltration to completely remove phospholipids. Phospholipids often cause strong immune reaction or side effects after blood transfusion. In this technique, the red blood cell was subject to controlled dialysis to gradually change the osmotic pressure thereof to prevent severe osmotic shock from red blood cells swelling. However, the dialytic procedure also made red blood cell membranes permeable to hemoglobin and would allow hemoglobin to be released from inside the red blood cell without rupturing the cell membrane. The dialyzed red blood cell solution was processed through a 0.1 µm pore to remove red blood cell membrane (or the so-called RBC-ghost) and obtain a phospholipid-free hemoglobin solution. This technique, however, does not remove other protein contaminants in the red blood cells.

More recently, Christensen et al., in an article entitled "Preparation of Human Hemoglobin Ao for Possible Use as A Blood Substitute," J. Biochemical and Biophysical Methods 17, 143–154 (1988), developed chromatographic methods for hemoglobin purification using anion-exchanger cellulose, such as DEAE, or cation-exchanger cellulose, such as CM. During the chromatographic separation, the pH or ionic strength of the eluent can be adjusted to control the type of proteins that can be eluted. Although this technique involves relative advanced technology, it is quite expensive and will not be economically justified unless the products have very high added value.

In 1990, Pristoupil used chloroform to extract hemoglobin. See, Pristoupil, et al., "Stroma-Free Hemoglobin Solutions Purified by Chloroform and Pasteurization", International Journal of Artificial Organs, vol. 13, no. 8, 383–387 (1990). Red blood cells, after being separated from plasma, was added to a separation phase containing sodium phosphate buffer (pH 7.5) and chloroform. The red blood cells were hemolyzed to release hemoglobin, which was then dissolved into the aqueous phase containing the phosphate buffer. The hydrophobic stroma and other non-heme proteins would precipitate in the chloroform phase. After charcoal adsorption and filtration through a 0.22 μm membrane, a purified hemoglobin can be obtained. The purification procedure can be achieved with a relatively high speed and simplicity. However, any residual chloroform can be toxic to the human body, and safety will always be a concern using the extraction technique.

SUMMARY OF THE PRESENT INVENTION

The primary object of the present invention is to develop an improved method for hemoglobin purification. More particularly, the primary object of the present invention is to develop a two-step dual-aqueous-phase extraction technique to separate hemoglobin from red cell membrane stroma and other protein contaminants, and thus obtain high purity hemoglobin. With the present invention, hemoglobin solution can be purified in a rapid, safe, non-toxic, and very economic manner.

The present invention does not require the filtration and centrifugation steps used in the prior art, thus significantly reduces the capital costs as well as the operation time and cost. Yet the present invention is extremely effective and can be easily scaled up for the mass production of purified hemoglobin at a very affordable cost.

The present invention involves a two-step extraction process. In the first step, a first dual-aqueous-phase liquid system is prepared. The upper aqueous phase of first dual-aqueous-phase liquid system comprises polyethylene glycol in water and the lower aqueous phase comprises a phosphate buffer at a pH of about 10. The hemoglobin solution to be purified is added to the first dual-aqueous-phase liquid system prepared above and stirred to achieve thorough mixing. Due to a higher partitioning coefficient of hemoglobin in the polyethylene glycol (PEG) solution relative to lower aqueous phase, hemoglobin will be extracted into the upper PEG phase.

Prior to the implementation of the purification process disclosed in the present invention, outdated blood from hospitals and/or animal bloods have been removed of their plasma by centrifugation, and the packed red blood cells (PRBCs) thus obtained were washed with saline. Pure water is added to the PRBCs to hemolyzed the red blood cells. The PRBC solution is then subject to a high speed homogenizer to further hemolyze the red blood cells and release hemoglobin contained therein.

In the second step, a second dual-aqueous-phase liquid system is prepared. The upper aqueous phase of the second dual-aqueous-phase liquid system comprises the polyethylene glycol phase containing the hemoglobin extracted in step 1, and the lower aqueous phase comprises a new phosphate buffer at a pH of less than 7.5. Due to a new set of partitioning coefficients in the new system, which favors the new phosphate salt solution, hemoglobin will be extracted from the upper (PEG) phase into the lower (phosphate salt) phase. After the second extraction step in the two step dual-aqueous-phase process, purified hemoglobin solution can then be obtained by removing the phosphate salt and the minute amounts of polyethylene glycol contained therein.

One of the main advantages of the method disclosed in the present invention is that it provides excellent result in the removal of stroma from red cell blood membranes (RBC ghosts) from the hemoglobin solution. It is well-known that the stroma contains mainly phospholipids, which, if present in the hemoglobin solution, can cause blood coagulation. No other prior art method is known to completely remove the red blood cell stroma.

Another main advantage of the method disclosed in the present invention is that the two phases involved in the extraction process are both aqueous phases. Thus the present invention is particularly suitable for the purification of hemoglobin that can be easily deactivated.

Yet another advantage of the present invention is its low or non-toxicity. It is well-known that both the polyethylene glycol and phosphate salts have little or non-toxicity. Therefore, no harm will be caused even if some polyethylene glycol and/or phosphate salts may still remain in the purified hemoglobin solution. Also, because both the polyethylene glycol and phosphate salts are relatively inexpensive materials, the present invention provides a safe and very economic way of purifying hemoglobin solution.

Furthermore, the present invention has an advantageous feature over the prior art methods in that the dual phases used in the present invention—the polyethylene glycol solution and the phosphate salt solution—have very low interfacial tension, about 0.1 dyne/cm. This characteristic, coupled with the low viscosity of both solutions—each solution is less than 50 cp—results in a very rapid mass transfer rate between the two phases and thus allows an equilibrium to be quickly achieved after a mixing between the two aqueous phases. Generally, an equilibrium can be achieved within several seconds after mixing. The present invention thus provides a very fast method to achieve hemoglobin purification.

Yet furthermore, because the dual-aqueous-phase extraction has been used in the separations industry, the present invention can utilize the past experience to develop industrial scale operations. The concept of using dual-aqueous-phase system was first disclosed by a Dutch microbiologist. In 1958, Albertsson applied the dual-aqueous-phase system in the extraction of polymers (P. Albertsson, "Particle Fractionation in Liquid Two-Phase Systems," *Biochimica et Biophysica ACTA*, 27 378–395 (1958). In 1978, Hustedt developed techniques for industrial large scale extraction using the dual-aqueous-phase system (H. Hustedt, et al., "Procedure for the Simultaneous Large-Scale Isolation of Pullulanase and 1,4-α-Glucan Phosphorylase from Klebsiella pneumoniae Involving Liquid-Liquid Separations," *Biotechnology and Bioengineering*, Vol XX, 1989-2005 (1978). The present invention thus presents a very viable approach to providing highly purified hemoglobin in a very economic manner.

BRIEF DESCRIPTION OF THE DRAWINGS

The file of this patent contains at least one drawing executed in color.

DETAILED DESCRIPTION OF THE PREFERRED EMBODIMENTS

Figure 1:
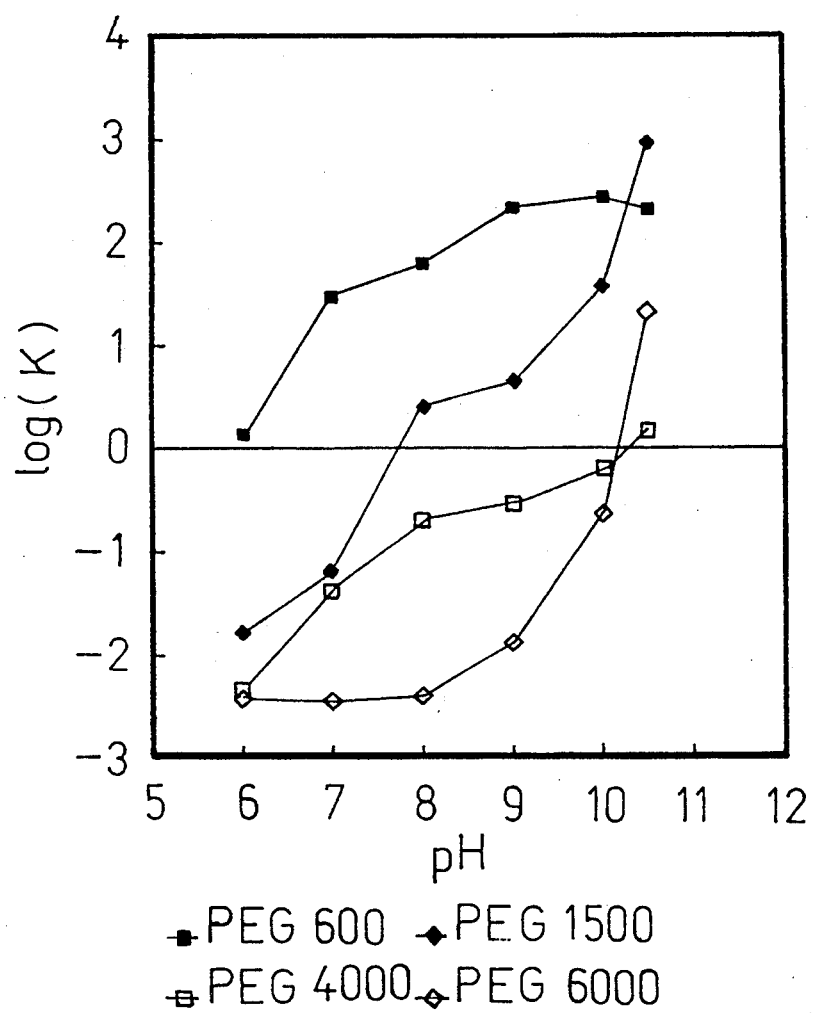
FIG. 1 shows the distribution coefficients of hemoglobin in a dual-aqueous-phase system containing a PEG solution of various molecular weight in the upper phase and a phosphate solution of various pit values in the lower phase.

In the process disclosed in the present invention, outdated human or animal bloods were first centrifuged then the plasma was removed. The PRBCs were washed with saline. Pure water was then added to the washed PRBCs to hemolyze the red blood cell. The PRBC solution was then subject to homogenization to further hemolyze the red blood cells and release the hemoglobin contained therein to form a hemoglobin solution.

A first dual-aqueous-phase liquid system was then prepared. The upper layer contained polyethylene glycol (PEG) in water, and the lower layer contained phosphate salt in water at a pH of 10.0. The hemoglobin solution prepared above was then added to the first dual-aqueous-phase liquid system, which was mixed to effect a first extraction procedure. During the first extraction step, hemoglobin and some contaminants were extracted into the upper PEG aqueous phase, while small amount of hemoglobin and the majority of the contaminants remained in the lower phosphate buffer aqueous phase and at the interface.

The upper PEG aqueous phase was then separated from the first dual-aqueous-phase liquid system and mixed with an appropriate phosphate salt solution to form a second dual-aqueous-phase liquid system. The phosphate salt solution in the second dual-aqueous-phase liquid system had a pH of below 7.5 and constituted the lower aqueous phase in the two-phase system, in co-existence with the upper PEG aqueous phase. The second dual-aqueous-phase liquid system was prepared to effect a second extraction procedure. During the second extraction step, essentially all the hemoglobin in the PEG solution was extracted into the lower phosphate salt aqueous phase, while the stroma remained in the upper PEG aqueous phase. After extraction, the lower phosphate buffer can be separated from the two-phase system to further remove the phosphate salt and minimal amount of PEG and obtain purified hemoglobin solution. Optionally, the hemoglobin solution can be concentrated and/or dialyzed to obtain purified hemoglobin solutions of appropriate concentrations.

The partitioning coefficient of a substance in the dual-aqueous-phase system is determined by a variety of parameters, such as: (1) the type of polymer used, (2) molecular weight and molecular weight distribution of the polymer, (3) phase composition, and (4) the type of salt added and the concentration thereof, (5) solution pH, and (6) temperature. In the method disclosed in the present invention, the above parameters can be adjusted to obtain the desired yield and purity, thus allows an excellent flexibility of operations. The present invention can also utilize a wide variety of animal bloods, such as human, bovine, pig bloods, etc. Optionally, an anti-coagulant, such as 10%, on a volumetric basis, of 3 g/l sodium citrate, can be added to the solution.

In the present invention, the molecular weight of the PEG is preferably between 1,000 and 8,000, or more preferably, about 1,500. The concentration of PEG in both the first and second dual-aqueous-phases is preferably between 10–25 wt %, or more preferably, between 15–20 wt %. The pH of the phosphate salt concentration in the first dual-aqueous-phase is preferably between 9.0–11.0, or more preferably about 10.0. Preferred phosphate salts in the first dual-aqueous-phase include potassium phosphate and sodium phosphate. The pH of the phosphate salt concentration in the second dual-aqueous-phase is preferably between 6.5–7.5, or more preferably about 7.0. Preferred phosphate salts in the second dual-aqueous-phase include potassium phosphate and sodium phosphate.

The dual-aqueous-phase extraction process disclosed in the present invention is relatively unaffected by the temperature and pressure of the system. Generally, it can be conducted under normal pressure and room temperature conditions.

In the present invention, the choice of the first and second dual-aqueous-phase can be optimized according to experiments obtained by varying the TLL, $V_t$, and the amount of red blood cells treated. The parameters are defined below.

$TLL(wt \%) = [(\Delta P)^2 + (\Delta S)^2]^{0.5}$;

$V_t$ = (upper phase volume)/(total volume);

$\Delta P$ = difference in PEG concentration between the upper and the lower phases;

$\Delta S$ = difference in phosphate salt concentration between the upper and the lower phases.

From extensive laboratory experiments, the optimum operation conditions for the dual-aqueous-phase are:

1. Under varying TLL conditions, maximum yield occurred at TLL=20–27 wt %. Maximum phospholipid removal occurred at TLL=21.9%; therefore, during the first dual-aqueous-phase extraction step, it was preferred to use TLL at 21.9%.

2. During the first dual-aqueous-phase extraction step, a higher value of $V_t$ resulted in greater yield. However, an important consideration is that there must be enough volume in the lower phase to contain cell stroma. Therefore, a $V_t$ value of 0.8 was preferred.

3. During the second dual-aqueous-phase extraction step, the value of TLL should be preferably small. However, because of the consideration that excess amount of PEG in the lower phase could affect the subsequent step of removing PEG and phosphate salt from the purified hemoglobin solution; therefore, it was preferred to conduct the purification at TLL=21.9 wt % during the second dual-aqueous-phase extraction step. Under these conditions, the concentration of PEG in the lower phase was 2.94 wt %, and the concentration of phosphate salt was 18.34 wt %.

4. During the second, dual-aqueous-phase extraction step, the value of $V_t$ had no effect on the yield and extent of purification. The value of $V_t$ can be appropriately adjusted according to the conditions of the subsequent dialysis or ultrafiltration steps.

The present invention will now be described more specifically with reference to the following examples. It is to be noted that the following descriptions of examples including preferred embodiments of this invention are presented herein for purpose of illustration and description; it is not intended to be exhaustive or to limit the invention to the precise form disclosed.

EXAMPLE 1

This example was conducted to demonstrate the relationship between the partitioning coefficients in the dual-aqueous-phase of PEG/phosphate salt solution and the molecular weight of PEG as well as the pH value of the phosphate salt solution.

Human blood was obtained from Hsinchu Provincial Hospital outdated blood. It was centrifuged to remove plasma, and was washed three times with a 0.9% saline solution to obtain packed red blood cells (Packed RBCs). Then the blood solution was subject to a homogenizer to hemolyze the red blood cells and obtain a highly concentrated hemoglobin solution.

A first dual-aqueous-phase system was prepared according to Table 1. Then the hemoglobin solution prepared above and the first dual-aqueous-phase system were added to a 15 g centrifuge tube. After mixing, the mixture was let to stand for 5 minutes, and was then centrifuged at 1,000 rpm for 10 minutes. In this system, the parameters were calculated to be: TLL=20 wt %, and $V_t$=0.5.

After phase separation, both the upper and the lower phases were removed respectively. The concentration of hemoglobin in each phase was measured by adding

TABLE 1

| Partitioning Coefficient, K | | | | |
|---|---|---|---|---|
| PEG solution: | | | | |
| Mw | 600 | 1,500 | 4,000 | 6,000 |
| conc. wt % | 16% | 12.5% | 12% | 10% |
| pH of phosphate salt solution: | | | | |
| 6 | 0.14 | −1.78 | −2.34 | −2.42 |
| 7 | 1.46 | −1.19 | −1.38 | −2.45 |
| 8 | 1.79 | 0.41 | −0.69 | −2.40 |
| 9 | 2.33 | 0.65 | −0.54 | −1.88 |
| 10 | 2.43 | 1.58 | −0.19 | −0.63 |
| 10.5 | 2.32 | 2.96 | 0.17 | 1.32 |

Drabkin's reagent to each phase to oxidize hemoglobin (Hb) and form CyanoMet Hb. By measuring light absorption at 540 nm of each separate phase, the concentration of hemoglobin was calculated. The following formula was used to calculate partitioning coefficient K in various dual-aqueous-phase systems.

K = (hemoglobin concentration in the upper phase)/(hemoglobin concentration in the upper phase)

Results of a series of experiments are listed in Table 1 and summarized in FIG. 1. From Table 1 and FIG. 1, it is shown that the partitioning coefficient of hemoglobin increases with the increased pH value in the lower aqueous phase. However, the relative values of the partitioning coefficient as well as the amount of their change are dependent on the molecular weight of PEG in the upper aqueous phase. In each set of samples, it can be clearly observed that in dual-aqueous-phase system containing the hemolysate with cell membranes, the stroma was concentrated in the lower phase as well as in the interface. Comparing the two phases, the upper was clear, while the lower phase was murky and nontransparent. After its being removed, the lower phase appeared to be gelatinous with an accumulation of cell stromal particles.

In this and following examples, PEG was purchased from Merck, Germany. The ingredients that were used in preparing the phosphate salt solution were also purchased from Merck. The phosphate salt solutions at various pH were prepared using titration method. The concentrations of phosphate salt solutions were 14.5%, 12.5%, and 9.5%, respectively.

EXAMPLE 2

This example illustrated a laboratory scale process of using the two-step dual-aqueous-phase system of the present invention to purify hemoglobin.

Figure 9:
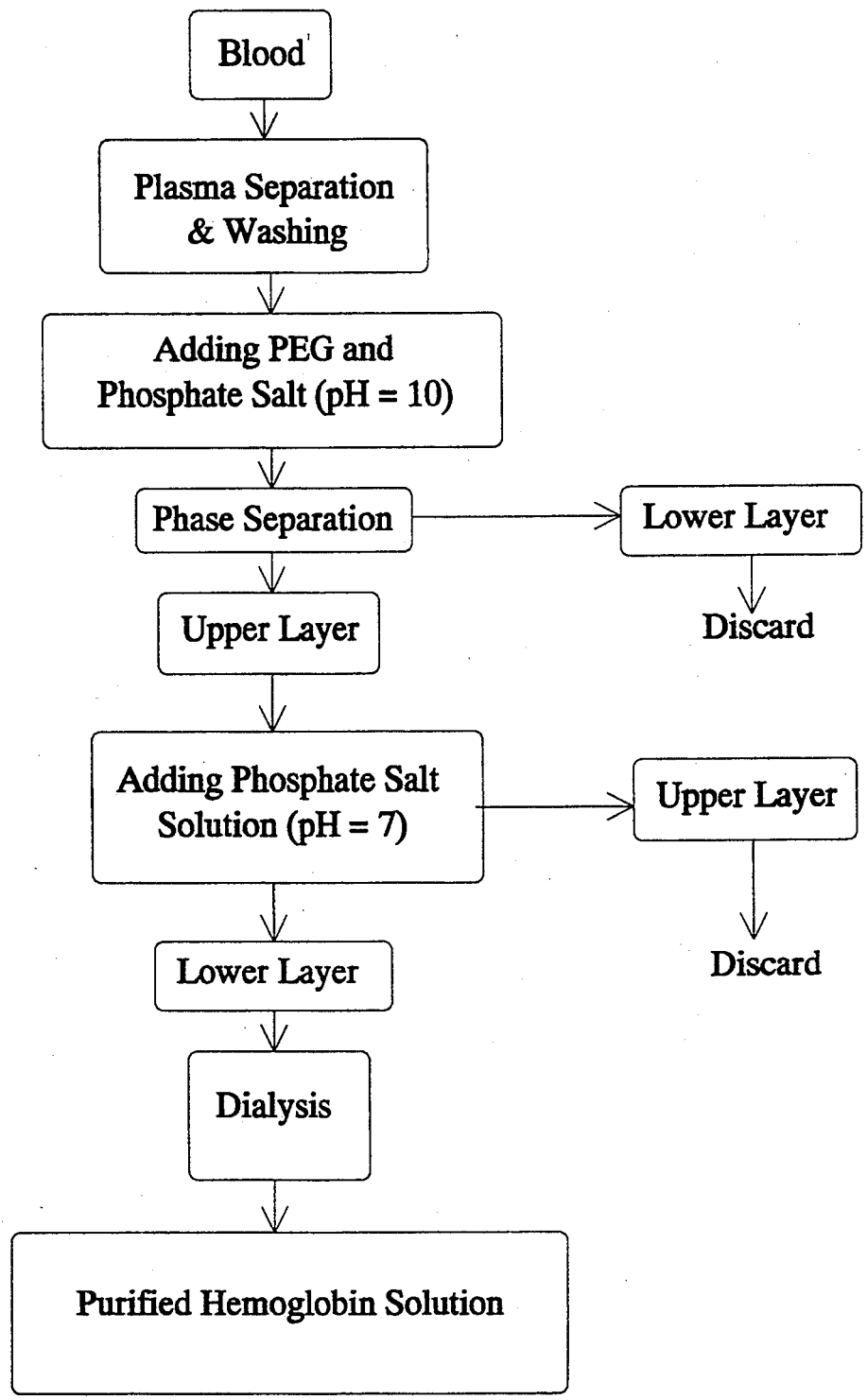
FIG. 9 is a flow chart of the steps involved in the hemoglobin purification process disclosed in the present invention.

20 ml of the highly concentrated hemoglobin solution obtained from Example 1 was subject to the purification process of the present invention according to the steps described in Table 2 and FIG. 9.

After the second dual-aqueous-phase extraction, the lower phase was removed and placed inside a dialysis bag (MWCO=6,000–8,000), which was then placed in a container containing 2 liters of either pure water or kidney dialysis solution for two days to remove phosphate salt solution and PEG. Finally, the hemoglobin solution was concentrated by subjecting the same under dialysis in a PEG 20,000 solution. During the concentrating step, the hemoglobin solution was placed inside a dialysis bag (MWCO=6,000–8,000), which was then put into a one-liter 30% PEG 20,000 solution for one day. The results from the concentrating step are also summarized in Table 2.

In Table 2, the definitions of the terms are provided below:

Yield from first extraction step (%) =

$$\frac{\text{hemoglobin content in the upper layer}}{\text{sum of hemoglobin content in the lower and upper layers}}$$

Yield from second extraction step (%) =

$$\frac{\text{hemoglobin content in the lower layer}}{\text{sum of hemoglobin content in the lower and upper layers}}$$

Recovery Ratio (%) =

$$\frac{\text{sum of hemoglobin content in the lower and upper layers}}{\text{total hemoglobin content before extraction}}$$

Net Yield (%) = (Yield) × (Recovery Ratio)

Total Net Yield (%) = (Net Yield from first extraction) × (Net Yield from second extraction)

To obtain yield, recovery ratio and net yield, the hemoglobin concentrations were first calculated according to the formula in Example 1, then the above equations were used in the calculation.

TABLE 2

|  | First Extraction | Second Extraction |
| --- | --- | --- |
| TLL, wt % | 22 | 22 |
| $V_t$ | 0.57 | 0.56 |
| K | 6.532 | $6.4 \times 10^{-4}$ |
| equilibrium time | 5 min. | 5 min. |
| phase separation time | 10 min. | 10 min. |
| centrifugation rpm | 1,000 × g | 1,000 × g |
| PEG Mw | 1,500 | 1,500 |
| PEG conc. | 18.9% | 15.5% |
| PEG volume | 48 ml | 36 ml |
| phosphate salt type | potassium salt | potassium and sodium salts |
| Phosphate salt conc. | 9% | 11% |
| pH | 10 | 7–7.5 |
| Phosphate salt volume | 35.7 ml | 28 ml |
| yield | 89.9% | 99.9% |
| recovery ratio | 58% | 100% |
| net yield | 52.1% | 99.1% |
| total net yield | 52% | |

During the first step in Example 2, hemoglobin was extracted into the upper PEG layer, then cell stroma, which were result of cell swelling or hemolysis, were concentrating in the lower phosphate salt phase and in the interface between the two phases. The purpose of this first step is to separate hemoglobin from phospholipids.

During the second step in Example 2, the upper layer PEG solution from step 1, which contained the majority of hemoglobin, was added to a lower layer phosphate salt solution at pH between 7 and 7.5. This caused hemoglobin to be extracted to the lower layer. The main purpose of this step was to achieve protein purification. During the first step, because of the high pH in the lower layer, most proteins, except those which had a strong tendency to remain in the lower layer or those which had a high pI value, would reside with hemoglobin in the PEG phase. The second extraction procedure removed those proteins which were likely to migrate to the upper phase or those with a lower pI value, by changing the pH of the extraction environment.

Figure 2:
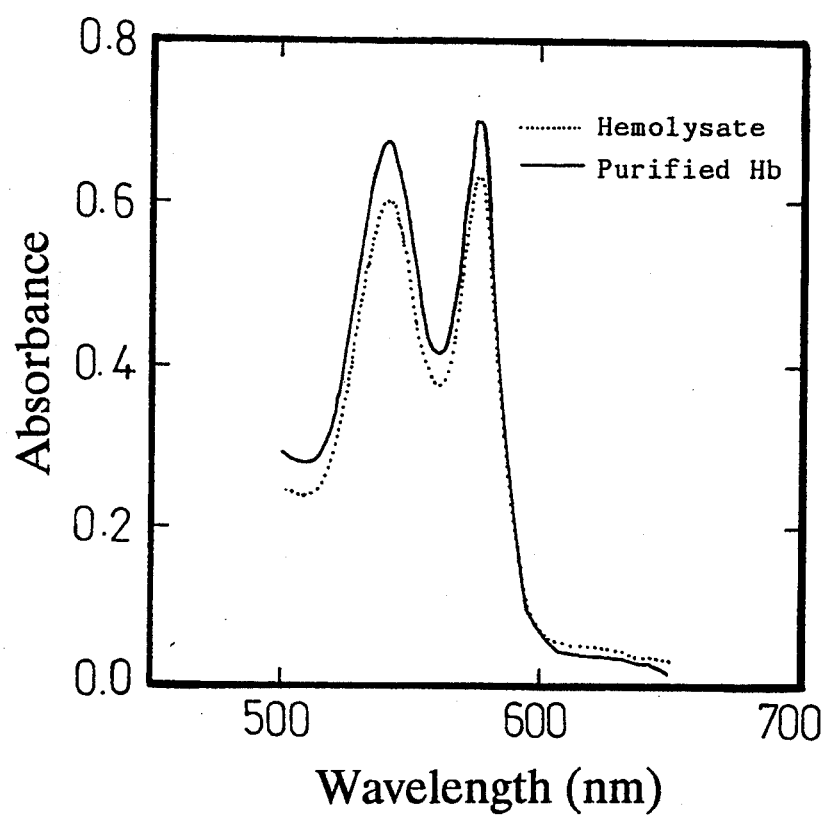
FIG. 2 shows the absorption spectrum of hemoglobin in the visible wavelength (500–600 nm) before and after purification.

Purified hemoglobin solution from this example was analyzed and reported in the following figures:

FIG. 2 shows the absorption spectrum of hemoglobin in the visible wavelength (500–600 nm) before and after purification. The analytical procedure was based on the method disclosed in "Method in Enzymology" 76, 54–133 (1981).

Figure 3:
FIG. 3 shows results from isoelectric point analysis of hemoglobin before and after purification (numeral 4 represents standard solution; numeral 3 represents hemoglobin solution before purification; numeral 2 represents hemoglobin solution after purification procedure of Example 2; numeral 1 represents hemoglobin solution after purification procedure of Example 1).

FIG. 3 shows results from isoelectric focusing (IEF) of hemoglobin before and after purification (numeral 4 represents standard solution; numeral 3 represents hemoglobin solution before purification; numeral 2 represents hemoglobin solution after purification procedure of Example 2; numeral 1 represents hemoglobin solution after purification procedure of Example 1). The analytical procedure was based on the method disclosed in "Phastsystem manual." Pharmarcia.

Figure 4:
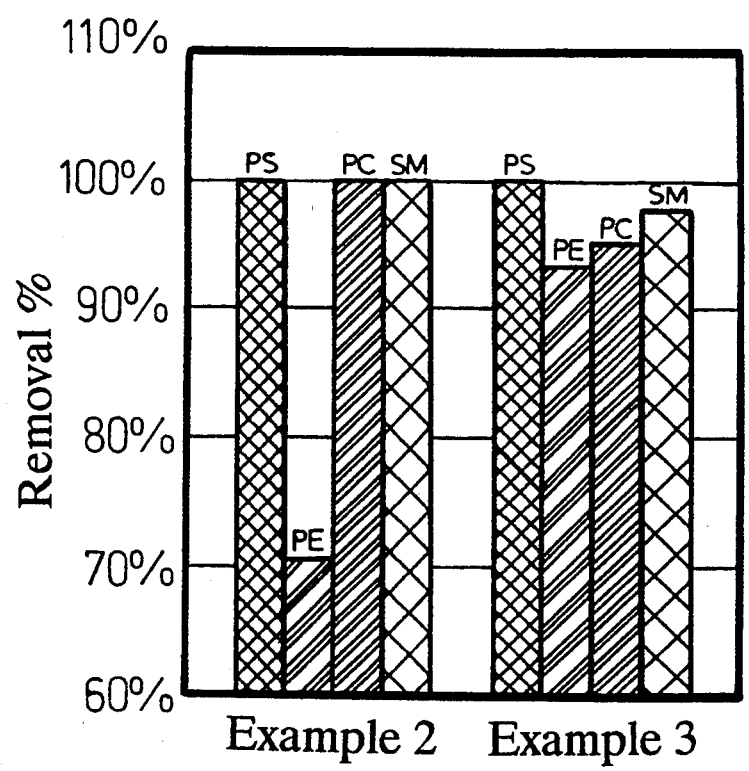
FIG. 4 shows the HPLC results of purified hemoglobin solutions from Examples 2 and 3 which show the effect of phospholipid removal (PS indicates phosphatidyl serine; PE indicates phosphatidyl ethanolamine; PC indicates lecithia; SM indicates sphingomyelin).

FIG. 4 shows the HPLC results of purified hemoglobin solutions from Examples 2 and 3, to show the effect of phospholipid removal (PS indicates phosphatidyl serine; PE indicates phosphatidyl ethanolamine; PC indicates lecithia; SM indicates sphingomyelin).

Figure 5:
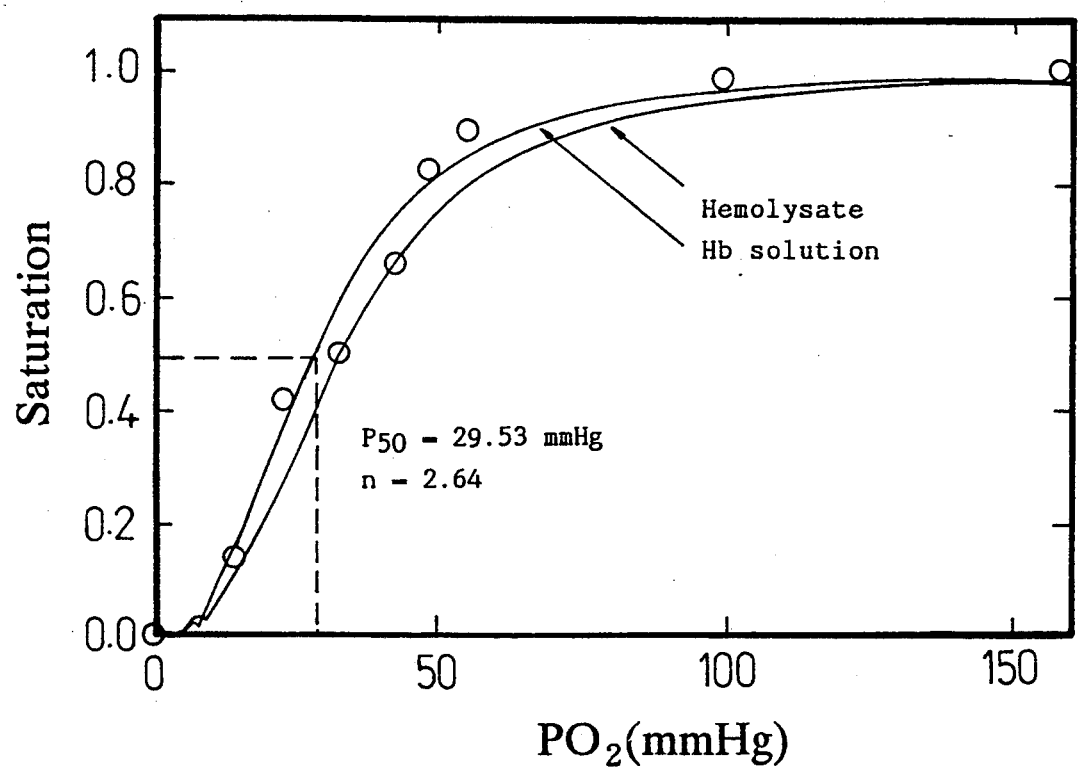
FIG. 5 shows the oxygen dissociation curve of hemoglobin solutions, before and after purification, at [Hb]=1.1 mg/ml, at 35° C. and 25% phosphate buffer solution (pH=7.4).

FIG. 5 shows the oxygen dissociation curve of hemoglobin, before and after purification, at [Hb]=1.1 mg/ml, at 37° C. and 25% phosphate buffer solution (pH=7.4). The analytical procedure was based on the method disclosed in Brittain, T. J., Chem. Edu., 59(3), 253–255 (1982).

FIG. 2 indicated no apparent change in the absorption spectrum was observed. The oxygen dissociation curves in FIG. 5 indicated the excellent oxygen carrying and releasing capacity of the purified hemoglobin from the process of the present invention.

Furthermore, IEF measurement results in FIG. 3 indicated that only residual amount of carbonic anhydrase (pI=6.3) existed in the purified hemoglobin solution; all other proteins were removed. In FIG. 4, which showed HPLC results, nearly all the phospholipids were removed after the two-step dual-aqueous-phase extraction process. The only exception was phosphatidylethanolamine, which showed a very minute but detectable residual in the purified solution. This indicated the excellent result of the process of the present invention in removing stromal particles.

EXAMPLE 3

Example 3 is a larger scale study of the purification procedure described in Example 2. 200 ml of red blood cells were purified. The only difference between Examples 2 and 3 was that, after the second step extraction, the dialysis method in Example 2 was replaced by an ultrafiltration technique. The operating conditions and results are summarized in Table 3.

Comparing Example 3 with Example 3, very little changes were observed in both the partitioning coefficients and the yield. This indicated the excellent potential for large scale operation of the present invention. Results of IEF and HPLC analyses, as shown in FIGS. 3 and 4, respectively, indicated no change in the removal of proteins and phospholipids in the scaled-up process. Large scale operation with ultrafiltration will significantly reduce the purification time per unit volume. In Example 3, the entire two-step dual-aqueous-phase extraction process took only about 2.5 hours to process 200 ml blood cells.

EXAMPLE 4

The experimental conditions in Example 4 were identical to those in Example 2, except that 3.8 g/dl sodium citrate was added to the bovine hemoglobin solution (100 ml sodium citrate solution per 900 ml fresh bovine blood). The experimental conditions and results therefrom are summarized in Table 4.

TABLE 3

| | First Extraction | Second Extraction |
|---|---|---|
| TLL, wt % | 22 | 22 |
| $V_t$ | 0.61 | 0.65 |
| K | 2.922 | $2.28 \times 10^{-4}$ |
| equilibrium time | 5–10 min. | 5–10 min. |
| phase separation time | 30 min. | 20 min. |
| centrifugation rpm | $5,000 \times g$ | $5,000 \times g$ |
| PEG Mw | 1,500 | 1,500 |
| PEG conc. | 18.9% | 15.5% |
| PEG volume | 521 ml | 370 ml |
| phosphate salt type | potassium salt | potassium and sodium salts |
| Phosphate salt conc. | 9% | 11% |
| pH | 10 | 7–7.5 |
| volume | 330 ml | 195 ml |
| yield | 82.2% | 99.9% |
| selectivity | 78.9% | 96.9% |
| net yield | 64.9% | 96.9% |
| total net yield | | 62.9% |

TABLE 4

| | First Extraction | Second Extraction |
|---|---|---|
| TLL, wt % | 22 | 22 |
| $V_t$ | 0.58 | 0.69 |
| K | 5.317 | $7.35 \times 10^{-4}$ |
| equilibrium time | 5–10 min. | 5–10 min. |
| phase separation time | 20 min. | 20 min. |
| centrifugation rpm | $1,000 \times g$ | $1,000 \times g$ |
| PEG Mw | 1,500 | 1,500 |
| PEG conc. | 18.9% | 15.5% |
| PEG volume | 26 ml | 19 ml |
| phosphate salt type | potassium salt | potassium and sodium salts |
| Phosphate salt conc. | 9% | 11% |
| pH | 10 | 7–7.5 |
| volume | 19 ml | 8.5 ml |
| yield | 87.9% | 99.8% |
| selectivity | 67.6% | 98% |
| net yield | 59.4% | 97.8% |
| total net yield | | 58.1% |

Figure 6B:
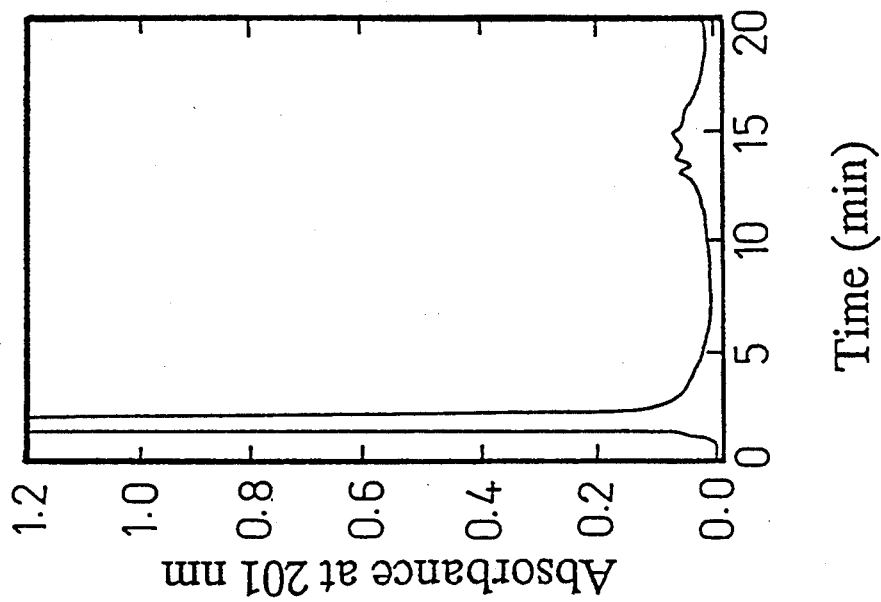
FIGS. 6a and 6b show, respectively, the results of phospholipid analysis of bovine hemoglobin solution before and after purification.
Figure 6A:
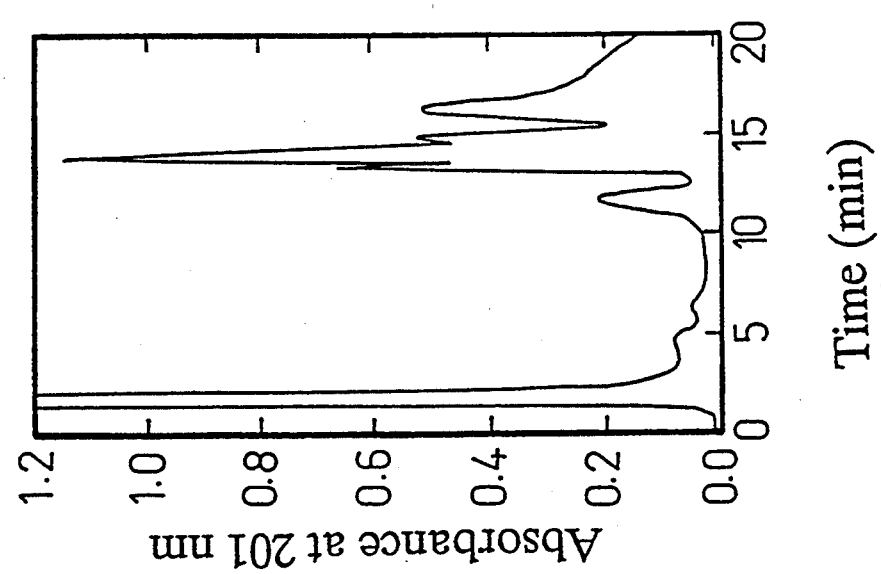
Figure 7:
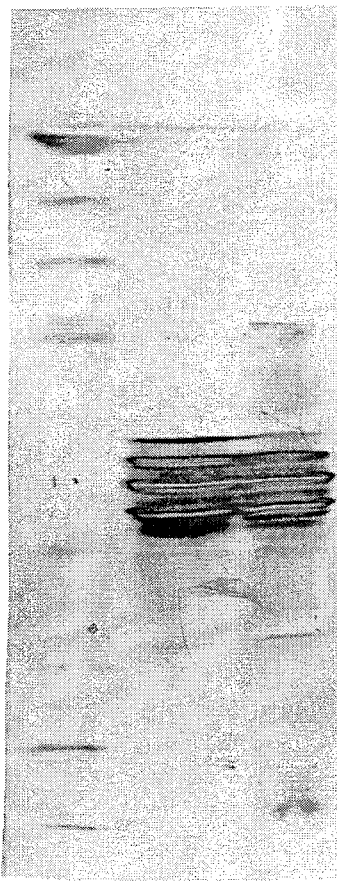
FIG. 7 shows results from isoelectric point analysis of bovine hemoglobin before and after purification (numeral 1 represents standard solution; numeral 2 represents bovine hemoglobin solution before purification; numeral 3 represents bovine hemoglobin solution after purification procedure of Example 2)

Data in Table 4 indicated that using dual-aqueous-phase extraction comparable results were obtained whether the process of the present invention was applied to human blood in Example 2, or to bovine blood in Example 4. FIGS. 6(a) and 6(b) showed, respectively, phospholipid analysis in bovine hemoglobin before and after the purification process. FIG. 7 showed, IEF results from the bovine hemoglobin before and after the purification process. All these data indicated excellent purification results of the two-step dual-aqueous-phase extraction process of the present invention.

COMPARATIVE EXAMPLES

Using bloods from the same source, hemoglobin solutions were purified using the following methods:
(A) Chloroform precipitation method (Pristoupil prior art);
(B) Chromatographic method (Christensen et al. prior art);
(C) High speed centrifugation method (Rabiner prior art);
(D) This method (Example 3).

Figure 8:
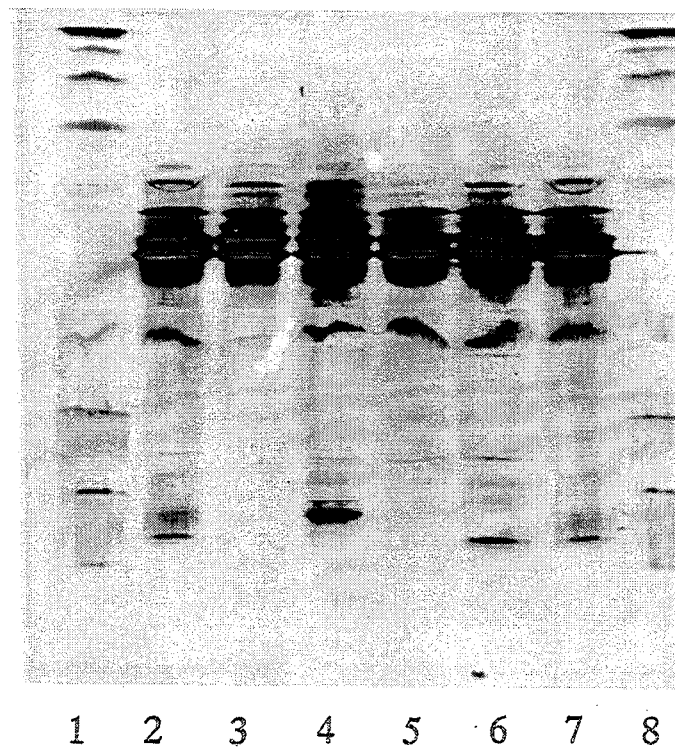
FIG. 8 shows results from isoelectric point analysis of bovine hemoglobin using various purification methods (numeral 3 indicates the dual-aqueous-phase method of the present invention; 4 indicates high-speed centrifugation method; 5 indicates DEAE-cellulose absorption method; 6 indicates chloroform precipitation method; 1 and 8 indicate standard solution; 2 and 7 indicate hemoglobin solution before purification).

FIG. 8 shows IEF analysis results from the purified hemoglobin solution obtained from the above listed methods. It is clear that the present invention provides the best purification result. Table 5 also summarized hemoglobin purification results from various methods. It further indicates that the present invention, which provides a new approach for hemoglobin purification, has the most promising potential in supplying blood substitute.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

TABLE 5

| | Purification Method | | | |
|---|---|---|---|---|
| | A | B | C | D |
| yield | 48.4% | 49% | 95% | 55% |
| operation time | 3 hours | 5 hours | 4 hours | 2.5 hours |
| purity | poor | good | very good | excellent |

What is claimed is:

1. A method to obtain purified hemoglobin solution comprising the steps of:
   (a) obtaining a supply of blood and hemolyzing red blood cells contained therein to release hemoglobin and form a hemoglobin solution;
   (b) subjecting said hemoglobin solution to a first extraction procedure to form a first extracted hemoglobin solution, said first extraction procedure employing a first dual-aqueous-phase liquid system, which comprises a first upper aqueous phase and a first lower aqueous phase, wherein said first upper aqueous phase comprising a first aqueous polyethylene glycol solution at a concentration between about 10 wt % and about 25 wt %, and said first lower aqueous phase comprising a first phosphate buffered aqueous solution at a pH of between about 9 and 11;
   (c) removing said first upper aqueous phase from said first extracted hemoglobin solution from step (b) and mixing said first upper aqueous phase, with a second phosphate buffered aqueous solution having a pH of between about 6.5 and about 7.5 to fore a second dual-aqueous-phase liquid system and effectuate a second extraction procedure, said second dual-aqueous-phase liquid system comprising a second upper aqueous phase and a second lower aqueous phase, wherein said second upper aqueous phase comprising a second aqueous polyethylene glycol solution, and said second lower aqueous phase comprising said second phosphate buffered aqueous solution at a pH between about 6.5 and about 7.5;
   (d) removing said second lower aqueous phase from said second dual-aqueous-phase liquid system; and (e) removing phosphate salt and minute amount of polyethylene glycol from said second lower aqueous phase.

2. The method to obtain purified hemoglobin solution according to claim 1 wherein said first phosphate buffered aqueous solution has a pH of about 10.

3. The method to obtain purified hemoglobin solution according to claim 1 wherein said polyethylene glycol has a molecular weight of between about 1,000 and 8,000.

4. The method to obtain purified hemoglobin solution according to claim 1 wherein said polyethylene glycol has a molecular weight of about 1,500.

5. The method to obtain purified hemoglobin solution according to claim 1 wherein said first aqueous polyethylene glycol solution contains 15 to 20 wt % polyethylene glycol.

6. The method to obtain purified hemoglobin solution according to claim 1 wherein said first extraction procedure comprises the steps of mixing said hemoglobin solution, said first upper aqueous phase and said first lower aqueous phase to form said first extracted hemoglobin solution; letting said first extracted hemoglobin solution stand for 5–10 minutes; and centrifuging said first extracted hemoglobin solution.

7. The method to obtain purified hemoglobin solution according to claim 1 wherein said second extraction procedure comprises the steps of mixing said first upper aqueous phase with said second phosphate buffered aqueous solution in order to form said second dual-aqueous-phase liquid system; letting said second dual-aqueous phase liquid system stand for 5–10 minutes; and centrifuging said second dual-aqueous phase liquid system.

8. The method to obtain purified hemoglobin solution according to claim 1 wherein said hemoglobin solution contains 10%, on a volummetric basis, of 3 g/l sodium citrate.

* * * * *